US00RE36892E

United States Patent [19]

Apffel, Jr. et al.

[11] E Patent Number: Re. 36,892

[45] Reissued Date of Patent: Oct. 3, 2000

[54] ORTHOGONAL ION SAMPLING FOR ELECTROSPRAY [LC/MS] MASS SPECTROMETRY

[75] Inventors: James A. Apffel, Jr., Mountain View; Mark H. Werlich, Santa Clara; James L. Bertsch, Palo Alto; Paul C. Goodley, Cupertino; Kent D. Henry, Newark, all of Calif.

[73] Assignee: Agilent Technologies, Palo Alto, Calif.

[21] Appl. No.: 08/792,303

[22] Filed: Jan. 31, 1997

Related U.S. Patent Documents

Reissue of:

[64] Patent No.: 5,495,108
Issued: Feb. 27, 1996
Appl. No.: 08/273,250
Filed: Jul. 11, 1994

[51] Int. Cl.[7] ..... B01D 59/46; H01J 49/00

[52] U.S. Cl. ..... 250/288

[58] Field of Search ..... 250/288, 288 A, 250/281

[56] References Cited

U.S. PATENT DOCUMENTS

| | | | |
|---|---|---|---|
| Re. 34,757 | 10/1994 | Smith | 250/288 |
| 3,867,631 | 2/1975 | Briggs et al. | 250/281 |

(List continued on next page.)

FOREIGN PATENT DOCUMENTS

| | | |
|---|---|---|
| 52-66488 | 1/1977 | Japan . |
| 59-845 | 1/1984 | Japan . |
| 1-146242 | 6/1989 | Japan . |
| 4-132153 | 5/1992 | Japan . |
| 6-060847 | 3/1994 | Japan . |
| WO 85/02490 A1 | 6/1985 | WIPO . |
| WO 95/24259 A1 | 9/1995 | WIPO . |

OTHER PUBLICATIONS

Apffel et al., "Gas–Nebulized Direct Liquid Introduction Interface for Liquid Chromatography/Mass Spectrometry", *Anal. Chem.*, 1983, vol. 55, p. 2280–2284 No Month.

Bruins et al., "Ion Spray Interface for Combined Liquid Chromatography/Atmospheric Pressure Ionization Mass Spectrometry", *Anal. Chem.*, 1987, vol. 59, p. 2642–2646 No Month.

Whitehouse et al., "Electrospray Interface for Liquid Chromatographs and Mass Spectrometers", *Anal. Chem.*, 1985, vol. 57, No. 3, p. 675–679 No Month.

Garcia et al., "Optimization of the Atmospheric Pressure Chemical Ionization Liquid Chromatography Mass Spectrometry Interface",*J. Am. Soc. Mass. Spectrom.*,1996, vol. 7, No. 1, p. 59–65. No Month.

Hagiwara et al., "Optimum Needle Materials of the Corona Discharge Electrode for Quantitative Analysis by Liquid Chromatography/Atmospheric Pressure Chemical Ionization–Mass Spectrometry", *J. Mass. Spectrom. Soc. Jpn.*, 1995, vol. 43, No. 6, p. 365–371. No Month.

Takada et al., "Atmospheric Pressure Chemical Ionization Interface for Capillary Electrophoresis/Mass Spectrometry", *Anal. Chem.*, Apr. 15, 1995, vol. 67, No. 8, p. 1474–1476.

(List continued on next page.)

*Primary Examiner*—Bruce C. Anderson

[57] ABSTRACT

[The invention teaches the uses of a plurality of electric fields and of orthogonal spray configurations of vaporized analyte which combine so as to operate to enhance the efficiency of analyte detection and mass analysis with a mass spectrometer by reducing vapor in the vacuum system and concomitant noise. Several embodiments of the invention are described for purposes of illustration.] *The invention relates to a method and apparatus for improving signal relative to noise without loss of ion collection efficiency in electrospray mass spectrometry, including liquid chromatography/mass spectrometry.*

67 Claims, 4 Drawing Sheets

U.S. PATENT DOCUMENTS

| | | | |
|---|---|---|---|
| 4,137,750 | 2/1979 | French et al. | 73/23 |
| 4,209,696 | 6/1980 | Fite | 250/281 |
| 4,300,044 | 11/1981 | Iribarne et al. | 250/282 |
| 4,531,056 | 7/1985 | Labowsky et al. | 250/288 |
| 4,542,293 | 9/1985 | Fenn et al. | 250/288 |
| 4,546,253 | 10/1985 | Tsuchiya et al. | 250/288 |
| 4,641,541 | 2/1987 | Sharp | 73/864.81 |
| 4,667,100 | 5/1987 | Lagna | 250/288 A |
| 4,746,068 | 5/1988 | Goodley et al. | 239/405 |
| 4,842,701 | 6/1989 | Smith et al. | 204/180.1 |
| 4,851,700 | 7/1989 | Goodley | 250/288 |
| 4,861,988 | 8/1989 | Henion et al. | 290/288 |
| 4,885,076 | 12/1989 | Smith et al. | 204/299 R |
| 4,935,624 | 6/1990 | Henion et al. | 250/288 |
| 4,960,991 | 10/1990 | Goodley et al. | 250/281 |
| 4,977,320 | 12/1990 | Chowdhury et al. | 250/288 |
| 4,977,785 | 12/1990 | Willoughby et al. | 73/863.12 |
| 4,982,097 | 1/1991 | Slivon et al. | 250/288 |
| 4,994,165 | 2/1991 | Lee et al. | 204/299 R |
| 4,999,493 | 3/1991 | Allen et al. | 250/288 |
| 5,015,845 | 5/1991 | Allen et al. | 250/288 |
| 5,030,826 | 7/1991 | Hansen | 250/288 |
| 5,051,583 | 9/1991 | Mimura et al. | 250/288 |
| 5,115,131 | 5/1992 | Jorgenson et al. | 250/288 |
| 5,122,670 | 6/1992 | Mylchreest et al. | 250/423 |
| 5,157,260 | 10/1992 | Mylchreest et al. | 250/423 |
| 5,162,650 | 11/1992 | Bier | 250/288 |
| 5,162,651 | 11/1992 | Kato | 250/288 |
| 5,170,053 | 12/1992 | Hail et al. | 250/288 |
| 5,171,990 | 12/1992 | Mylchreest | 250/288 |
| 5,223,226 | 6/1993 | Wittmer et al. | 422/100 |
| 5,235,186 | 8/1993 | Robins | 250/288 |
| 5,245,186 | 9/1993 | Chait et al. | 250/288 |
| 5,247,842 | 9/1993 | Kaufman et al. | 73/865.5 |
| 5,285,064 | 2/1994 | Wiloughby | 250/288 |
| 5,289,003 | 2/1994 | Musser | 250/288 |
| 5,304,798 | 4/1994 | Tomany et al. | 250/288 |
| 5,306,412 | 4/1994 | Whitehouse et al. | 204/299 |
| 5,331,160 | 7/1994 | Whitt | 250/288 |
| 5,349,186 | 9/1994 | Ikonomou et al. | 250/288 |
| 5,376,789 | 12/1994 | Stenhagen | 250/288 |
| 5,393,975 | 2/1995 | Hail et al. | 250/288 |
| 5,406,079 | 4/1995 | Kato | 250/288 |
| 5,412,208 | 5/1995 | Covey et al. | 250/288 |
| 5,416,322 | 5/1995 | Chace et al. | 250/288 |
| 5,423,964 | 6/1995 | Smith et al. | 204/180.1 |
| 5,436,446 | 7/1995 | Jarrell et al. | 250/288 |
| 5,481,107 | 1/1996 | Takada et al. | 250/281 |
| 5,505,832 | 4/1996 | Laukien et al. | 204/452 |
| 5,559,326 | 9/1996 | Goodley et al. | 250/288 |

OTHER PUBLICATIONS

Doerge et al., "Multiresidue Analysis of Sulfonamides Using Liquid Chromatography with Atmospheric Pressure Chemical Ionization Mass Spectrometry", *Rapid Communications in Mass Spectrom.*, Dec. 1993, vol. 7, No. 12, p. 1126–1130.

Willoughby et al., "Monodisperse Aerosol Generation Interface for Combining Liquid Chromatography with Mass Spectroscopy", *Anal. Chem.*, 1984, vol. 56, p. 2626–2631 No Month.

Yamashita et al., "Electrospray Ion Source. Another Variation on the Free–Jet Theme", *J. Phys. Chem.*, 1984, vol. 88, p. 4451–4459.

Kambara et al., "Ionization Charateristics of Atmospheric Pressure Ionization by Corona Discharge", *Mass Spectroscopy*, Sep. 1976, vol. 24, No. 3, p. 229–236.

Lee et al., "Real–Time Reaction Monitoring by Continuous–Introduction Ion–Spray Tandem Mass Spectrometry", J. Am. Chem. Soc., 1989, vol. III, No. 13, p. 4600–4604.

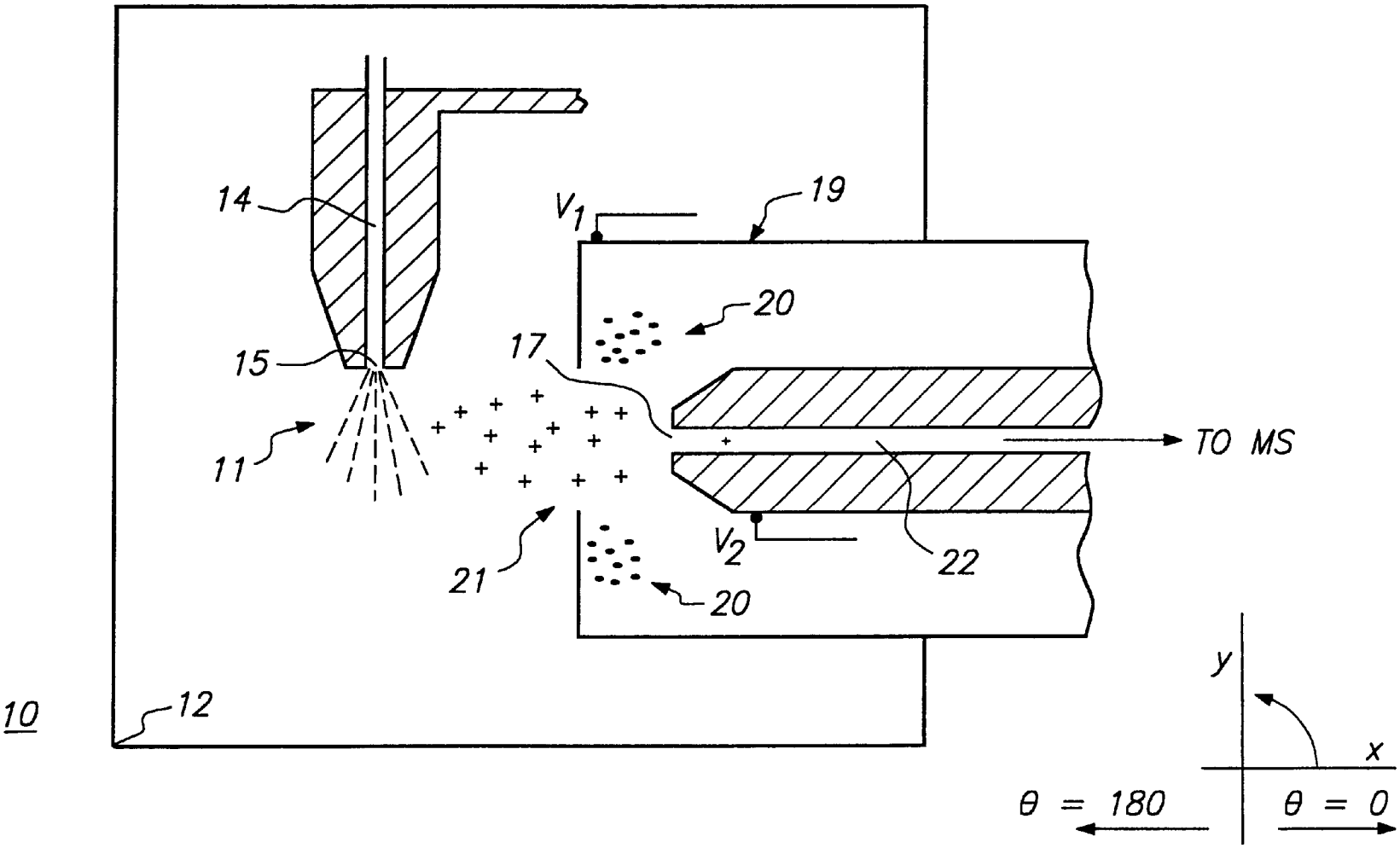
AMENDED FIG. 1

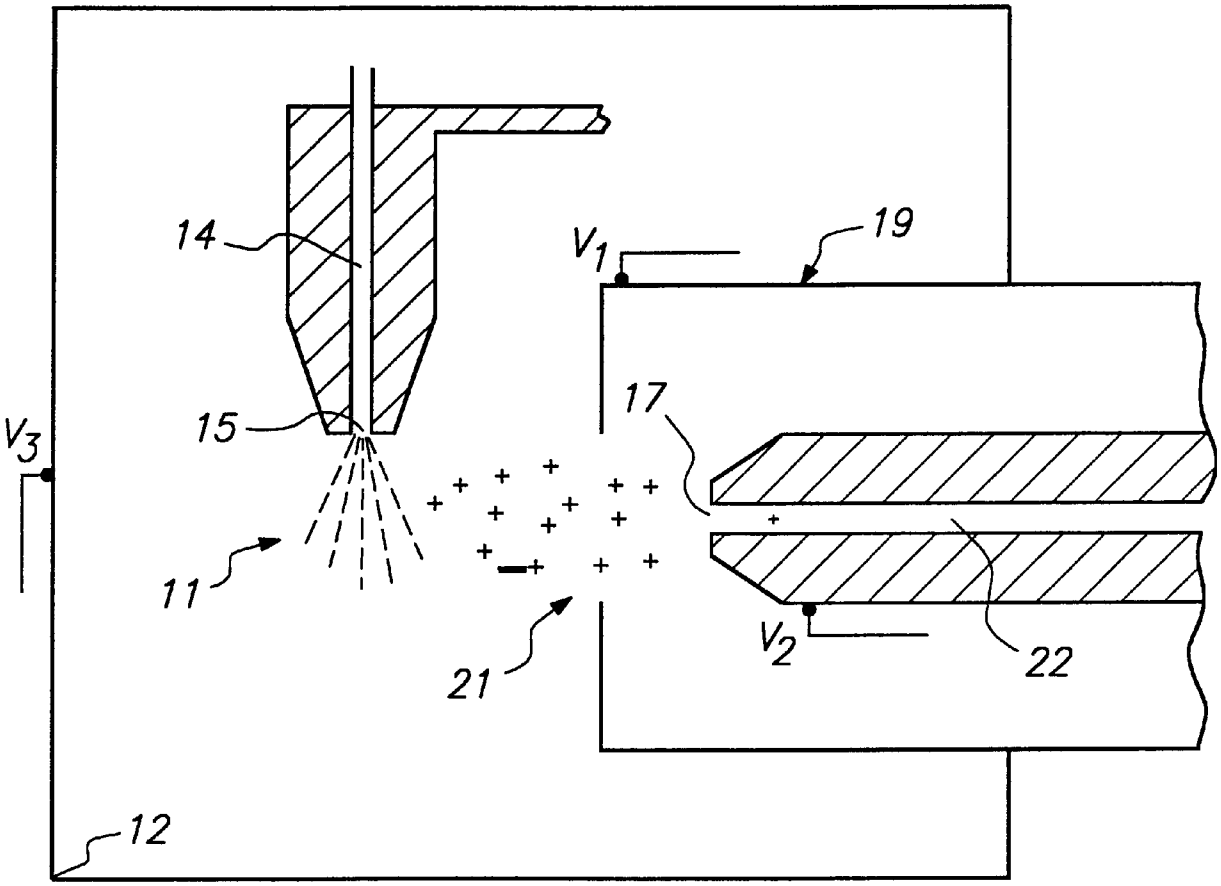
AMENDED FIG. 2

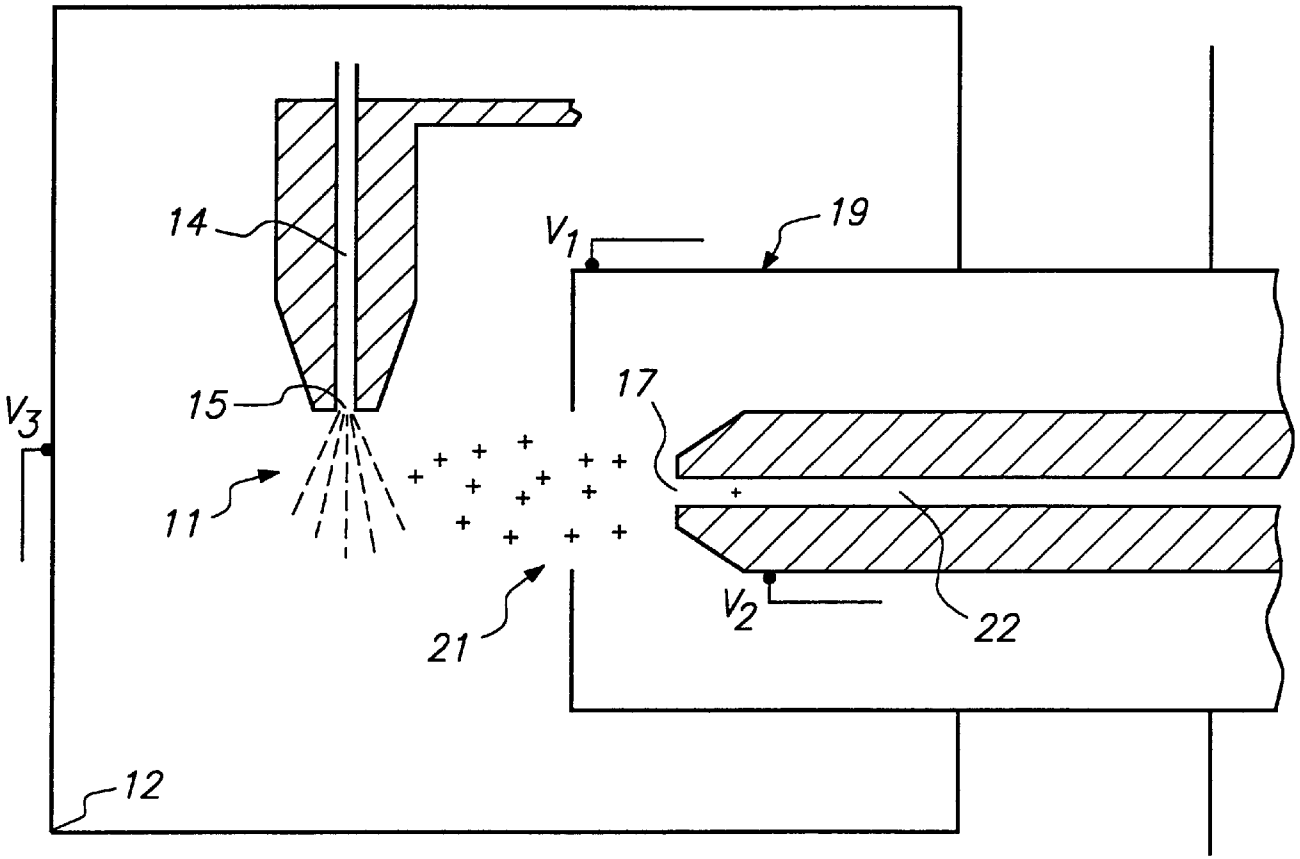
AMENDED FIG. 3

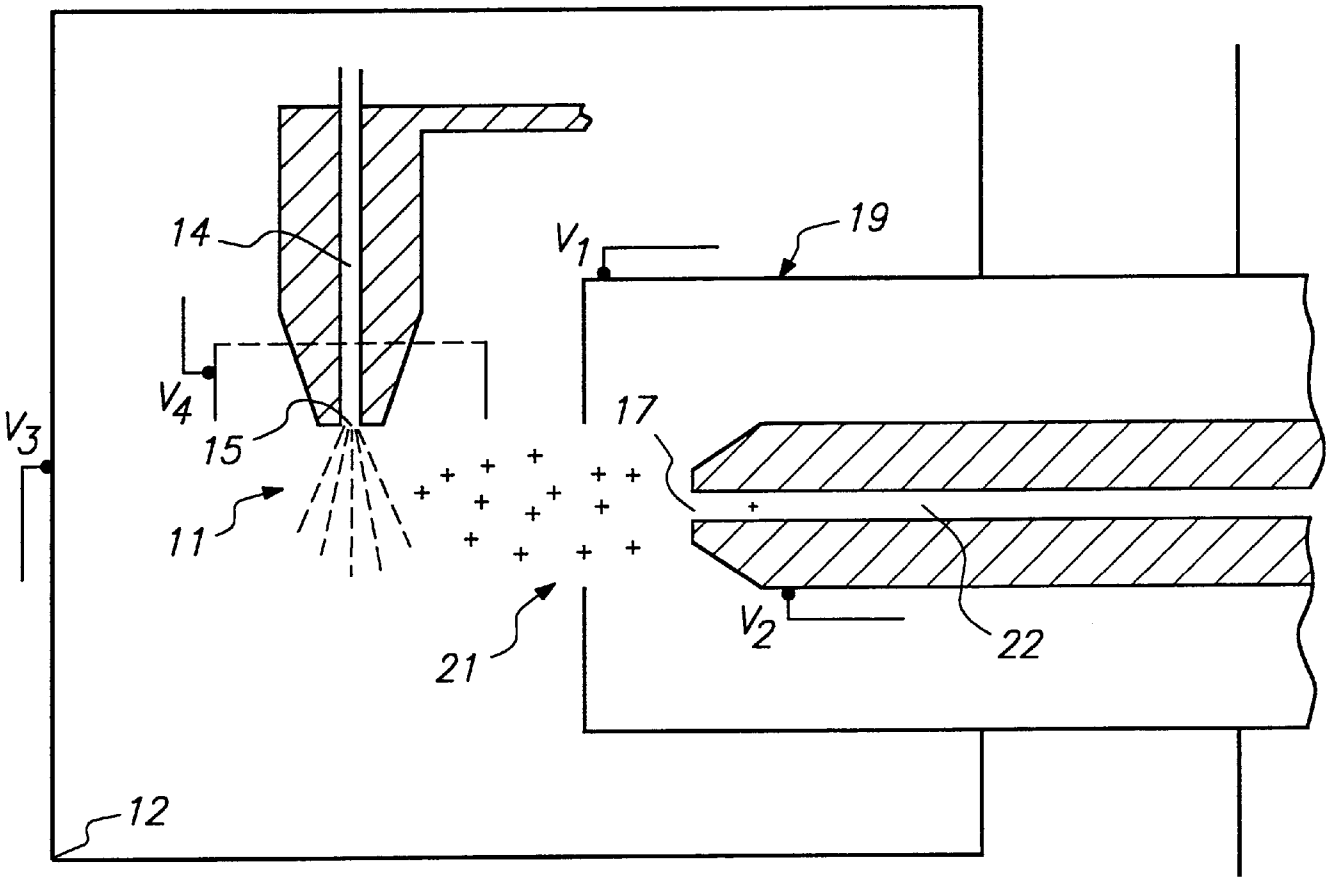
AMENDED FIG. 4

ORTHOGONAL ION SAMPLING FOR ELECTROSPRAY [LC/MS] MASS SPECTROMETRY

Matter enclosed in heavy brackets [ ] appears in the original patent but forms no part of this reissue specification; matter printed in italics indicates the additions made by reissue.

INTRODUCTION

The invention relates to a method and apparatus for obtaining improved *signal relative to noise without loss of* ion collection efficiency in electrospray [on] *mass spectrometry, including liquid chromatography/mass spectrometry* (LC/MS).

Initial systems for electrospray LC/MS utilized flow splitters that divided the HPLC (*high performance liquid chromatography*) column effluent in such a way that a small portion, typically 5–50 micro liters per minute, was introduced into the "spray chamber", while the major portion was directed to a waste or fraction collector. Because *these* low flow rates were introduced into electrospray (*ES*) *mass spectrometry* (*MS*) systems, it became possible to generate [spray] *electrosprayed aerosol* solely through the use of electrostatic forces. Since ES/MS [is] *generally provides* a concentration sensitive detector, this does not result in loss of sensitivity when compared with introduction of all the flow *from the HPLC column effluent* into the spray chamber (assuming equal charging and sampling efficiencies). However, the use of flow splitters has gained a bad reputation due to potential plugging problems and poor reproducibility.

Newer electrospray systems generate a charged [spray] *or ionized aerosol* through the combination of electrostatic forces and [an] assisted nebulization. The assisted nebulization *generally* generates an aerosol from the HPLC *column* effluent, while the electric field induces a charge on the droplets, which ultimately results in the generation of desolvated analyte ions via an ion evaporation process. The assisted nebulization can be done with pneumatic, ultrasonic, or thermal nebulization or by some other nebulization technique.

In each of these newer assisted nebulizer systems, it has been necessary to design the system so that the solvated droplets present in the *electrosprayed* aerosol do not enter the vacuum system. This has been accomplished in several ways.

*In conventional electrospray/nebulization mass spectrometry systems, the electrosprayed aerosol exiting from the nebulizer is sprayed directly towards the sampling orifice or other entry into the vacuum system such as a capillary. That is, the electrosprayed aerosol exiting from the nebulizer and the entry into the vacuum system are located along a common central axis, with the nebulizer effluent pointing directly at the entry into the vacuum system and with the nebulizer being considered to be located at an angle of zero (0) degrees relative to the common central axis.*

[In one currently available system,] *One previous approach directed at improving performance adjusts the aerosol to spray "off-axis". That is,* the aerosol is sprayed ["off axis"] *"off-axis"* at an angle of as much as 45 degrees with respect to the *central* axis of the sampling orifice. In addition, a counter current [drying] gas is [sprayed] *passed* around the sampling orifice to blow the solvated droplets away from the orifice. The gas [pressures] *velocities* typically used [generates] *generate* a plume of small droplets and optimal performance appears to be limited to a flow rate of 200 microliters per minute or lower.

In another currently available system, an aerosol is generated pneumatically and aimed directly at the entrance of a heated capillary tube *providing a passageway* into the vacuum system. Instead of desolvated ions entering the capillary, large charged droplets are drawn into the capillary and the droplets are desolvated while in transit. The evaporation process takes place in the capillary as well. A supersonic jet of vapor exits the capillary and the analyte ions are subsequently focused, mass analyzed and detected. There are several disadvantages to this system. The use of the high temperature capillary may result in thermal degradation of thermally labile samples. In the supersonic jet expansion, the desolvated ions and vapor may recondense, resulting in solvent clusters and background signals. While these clusters may be re-dissociated by collisionally induced processes, this may interfere in identification of structural characteristics of the analyte samples which are intentionally subjected to collisionally induced dissociation. The large amount of solvent vapor, ions and droplets exiting the capillary require that the detector be arranged substantially [off axis] *off-axis* with respect to the capillary to avoid noise due to neutral droplets striking the *mass analyzer and* detector. The additional solvent entering the vacuum *system* requires larger *capacity* pumps.

In another currently available system, the [spray] *electrosprayed aerosol* is generated ultrasonically. The system is used in conjunction with a counter current drying gas and is usually operated with the [spray] *aerosol* directed at the sampling capillary. The main disadvantages of this system, from the practitioner's point of view, are that optimal performance is effectively limited to less than 500 microliters per minute and [that] there are serious problems with aqueous mobile phases. Furthermore, the apparatus is complex and prone to mechanical and electronic failures.

In another commonly used system, a pneumatic nebulizer is used at substantially higher inlet pressures (as compared with other systems). This results in a highly collimated and directed [droplet beam] *electrosprayed aerosol.* This *aerosol* is aimed off-axis to the side of the orifice [in] *and at* the nozzle cap. Although this works competitively, there is still some noise which is probably due to stray droplets. The *aerosol exiting the* nebulizer [jet] has to be aimed carefully to minimize noise while maintaining signal intensity.

SUMMARY OF INVENTION

*The invention relates to an apparatus for converting a liquid solute sample into ionized molecules, comprising:*

*a first passageway having a center axis, an orifice for accepting a liquid solute sample and an exit for discharging the liquid solute sample from the first passageway in the form of an electrosprayed aerosol containing ionized molecules;*

*an electrically conductive housing connected to a first voltage source and having an opening arranged adjacent to the first passageway exit; and*

*a second passageway arranged within the housing adjacent to the opening in the housing and connected to a second voltage source, the second passageway having a center axis, an orifice for receiving ionized molecules attracted from the electrosprayed aerosol and an exit, wherein the center axis of the second passageway is arranged in transverse relation to the center axis of the first passageway such that ionized molecules in the electrosprayed aerosol move laterally through the*

*opening in the housing and thereafter pass into the second passageway under the influence of electrostatic attraction forces generated by the first and second voltage sources.*

The invention provides the capability of conducting atmospheric pressure ionization[,] (API), whether electrospray or atmospheric pressure chemical ionization (APCI), with conventional [High Performance Liquid Chromatography] *high performance liquid chromatography* at flow rates of greater than 1 ml/minute without flow splitting. The invention allows desolvated ions to be separated from comparatively large volumes of [vaporized] *electrosprayed* column effluent, and then, while keeping out as much of the solvent as possible, introducing the desolvated ions into the vacuum system for mass detection and analysis [while introducing as little of the solvent as possible]. The invention provides the capability of separating desolvated ions of interest from the large volumes of vapor[,] and directing the desolvated ions from the electrospray (ES) chamber (which *typically* operates at atmospheric pressure) to the mass spectrometer (which operates at $10^{-6}$ to $10^{-4}$ [Torr] *torr*). The *orthogonal* selection *process* allows the introduction of ions without overwhelming the vacuum system and without sacrificing the sensitivity of the system, [because] *since* the maximum amount of analyte is introduced into the vacuum system for mass analysis and detection.

Orthogonal ion sampling according to the present invention allows more efficient enrichment of the analyte by spraying the charged droplets *in the electrosprayed aerosol* past a sampling orifice, while directing the solvent vapor and solvated droplets *in the electrosprayed aerosol* away [in a direction such] *from the sampling orifice so* that they do not enter the vacuum system.

The noise level in [an] *a mass spectrometry* apparatus configured according to the present invention is reduced by as much as five fold over current systems, resulting in increased signal relative to noise, *and* hence[,] *acheiving* greater sensitivity. Performance is simplified and the system *is* more robust because optimization of [needle] *the* position *of the first passageway*, gas flow and voltages show less sensitivity to small changes. The simplified performance and reduced need for optimization also result in a system less dependent [of] *on* flow rate and mobile phase conditions. The reduced need for optimization extends to changing mobile phase flow rates and proportions. This means that the *mass spectrometry* system can be run under a variety of conditions without adjustment.

Another benefit of the invention taught herein is simplified waste removal owing to the fact that the [spray] *electrosprayed aerosol* can be aimed directly at a waste line and be easily removed from the system. Furthermore, the present invention provides the option of eliminating high voltage elements with no loss of sensitivity.

BRIEF DESCRIPTION OF THE DRAWINGS

FIG. 1 is a representation of an apparatus according to the present invention.

FIG. 2 is a representation of an alternate embodiment of an apparatus according to the present invention.

FIG. 3 is a representation of an alternate embodiment of an apparatus according to the present invention.

FIG. 4 is a representation of an alternate embodiment of an apparatus according to the present invention.

DETAILED DESCRIPTION OF THE INVENTION

FIG. 1 depicts an apparatus 10 configured according to the current invention. As in conventional sample introduction, a liquid sample is conducted through [the] *a* nebulizer [with] *having* a first passageway 14, *the liquid sample* exiting a second orifice or exit *15* of the first passageway [15] *14* under conditions which create a vapor of charged *or ionized* droplets or ["electrospray"] *electrosprayed aerosol* 11. The invention provides a rather different electrospray particle transport as compared with conventional electrospray *processes*. FIG. 1 depicts the transport of the [electrospray] droplets *in the electrosprayed aerosol 11* from the second orifice exit *15* of the first passageway [15] *14*, through the distance to the entrance *or opening 17* of the second passageway [17] *22*, and entering the second passageway [18] *22* where the orientation angle θ of the *center* axis of the exiting [electrospray] *electrosprayed aerosol* 11 and *the center axis of* the second passageway 22 is between 75 degrees and 105 degrees relative to each other. The angle may be greater than 105, in principle as great as 180; best results have been obtained at settings at or near 90 degrees. (*As shown in FIG. 1, the angle θ defines the location of the first passageway 14, that is, the nebulizer or other source of electrosprayed aerosol 11, relative to the second passageway 22, that is, the entry into the vacuum system. The angle θ is considered to be zero (0) degrees when the exit 15 for the electrosprayed aerosol 11 and the center axis of the first passageway 14 are pointing directly at the entrance 17 and the center axis of the second passageway 22. The angle θ is considered to be 180 degrees when the exit 15 for the electrosprayed aerosol 11 and the center axis of the first passageway 14 are pointing directly away from the entrance 17 and the center axis of the second passageway 22*). The charged droplets *forming the electrosprayed aersol 11* are electrostatically attracted laterally across the gap between the exit *15* of the first passageway [15] *14* into the opening *17* of the second passageway [17] *22*. The electrostatic attraction is generated by attaching voltage sources to components of the apparatus. A first voltage source [16] *V1* is connected to a housing 19 which houses the second passageway 22. The housing *19* is not necessarily an enclosure but may be [in] any shape that can act as a guide for the ions and can support fluid dynamics of a drying gas (see below discussion). A second voltage source [18] *V2* is connected to the second passageway 22. The first passageway 14 is generally kept at ground *potential*.

In the course of crossing the gap and approaching the entrance *17* to the second passageway 22, especially after passing through an opening 21 in the housing 19 containing the second passageway 22, the [electrospray] *electrosprayed aerosol* is subjected to the cross flow of a gas 20—a condition that operates to remove solvent from the droplets, thereby leaving [small] charged [droplets] *particles or ions*. The [small droplets] *ions* are amenable to analysis by operation of an analytic instrument capable of detecting and measuring mass and charge of particles such as a mass spectrometer (not shown). The second passageway *22* exits into the mass spectrometer or equivalent instrument.

A standard electrospray *MS* system (HP 5989) with a pneumatic nebulizer provides the base structure. A spray box 12 of plexiglass or some other suitable material for preventing shock and containing noxious vapors replaces the standard spray chamber. Within the spray box 12, the nebulizer *containing the first passageway* 14 may be arranged in a variety of configurations, so long as the [distance] *distances* between the separate high voltage [points is] *sources are* sufficient to prevent discharges. Additional surfaces at high voltage may be used to shape the electrical fields experienced by the [spray] *electrosprayed aerosol*. In the embodiment depicted in FIG. 1, the system includes a [drying] gas

20 to aid desolvation and prevent [spray] droplets *in the electrosprayed aerosol* 11 from entering the [orifice] *opening 17* of the second passageway [17] *22* and the vacuum system (not shown). An alternate embodiment could include a heated capillary as the second passageway 22 in an internal source off-axis geometry, such that the capillary is off-axis with respect to [quadropole] *the analyzer* (*such as a quadrupole*) and detector components.

The *positive ion* configuration shown in FIG. 1 [generally] *typically* has the second voltage source [18] *V2* set [typically] at −4.5 kV, [and] the first voltage source [16] *V1 set* at −4 kV, and the first passageway 14 generally comprising a needle *set* at ground *potential*. Gas, usually nitrogen at nominally 200 degree to 400 [degree] *degrees* Centigrade and approximately 10 standard [liter] *liters* per minute, is typically used as a cross flow [drying] gas *20*, although other gases can be used. The [drying] gas 20 flows across the aperture at approximately 90 degrees to the axis of the [incoming] charged molecules *in the electrosprayed aerosol*.

The term "passageway", as used [in this application] *herein with respect to the second passageway*, means "ion guide" in any form [whatever] *whatsoever*. It is possible that the passageway [be] *is* of such short length relative to *the* opening diameter that it may be called an orifice. Other ion guides, including capillaries, which are or may come to be used, can operate in the invention. The configurations herein are not meant to be restrictive, and those skilled in the art will see possible configurations not specifically mentioned here but which are included in the teaching and claims of this invention.

EXAMPLES

A number of different configurations have [proved] *been proven* possible. Examples of certain tested configurations follow.

FIG. 2 shows a configuration of the invention in which a third voltage source, [a plate 29] *V3,* is positioned beside the exit *15* of the first passageway [15] *14* and distal to the side near to which the first voltage source [16] *V1* and opening *17* to the second passageway [cavity 17] *22* are positioned. The [plate 29 runs] *third voltage source V3 provides* a positive voltage relative to the first voltage source [16] *V1*. Experiments show *that* the [charged droplet electrospray] *electrosprayed aerosol* "sees" a mean voltage between the plate [29] *24* and the charged housing 19. Results suggest that the repeller effect may be captured and ion collection yield increased by careful sculpting of both the electric field and the gas flow patterns.

FIG. 3 shows a two voltage source system as in FIG. 2 [with the addition of a grounded spray chamber 26] *wherein V3 is at ground potential*. The spray chamber 26 operates to contain the *electrosprayed* aerosol and route condensed vapor to waste.

FIG. 4 shows the addition of a ring-shaped electrode [28] *or fourth voltage source V4* encircling the [flow] *electrosprayed aerosol* exiting from the needle or first passageway 14 at ground, with all of the elements configured as in FIG. 3. The ring-shaped electrode [28] *or fourth voltage source V4* induces a charge in the droplets by virtue of the potential difference in charge between the droplets and the ring-shaped electrode [28] *or fourth voltage source V4*. Other potentials in the system can be used to direct the sampling of ions.

What is claimed is:

1. An apparatus for converting a *liquid* solute [sampled] *sample* into ionized molecules, comprising:

a first passageway having a center axis, an orifice for accepting a *liquid* solute sample and an exit for discharging the *liquid solute* sample from the *first* passageway in the form of an [electrospray] *electrosprayed aerosol* containing [charged] *ionized* molecules;

an electrically conductive housing connected to a first voltage source and having an opening arranged adjacent to the first passageway exit; and a second passageway arranged within the housing adjacent to the opening *in the housing* and connected to a second voltage source, the second passageway having a center axis, an orifice for receiving [charged] *ionized* molecules attracted from the [electrospray] *electrosprayed aerosol* and an exit, wherein the center axis of the second passageway is arranged in transverse relation to the center axis of the first passageway such that [charged] *ionized* molecules in the [electrospray] *electrosprayed aerosol* move laterally through the opening in the housing and thereafter pass into the second passageway under the influence of electrostatic attraction forces generated by the first and second voltage sources*; wherein an angle formed between the center axis of the first passageway and the center axis of the second passageway is between about 75 degrees and 105 degrees*.

2. The apparatus of claim 1 wherein [an] *the* angle formed between the center axis of the first passageway and the center axis of the second passageway is [greater than 75 degrees and less than or equal to 180] *about 90* degrees.

3. The apparatus of claim [2] *1* further comprising means for directing a stream of a drying gas in front of the orifice of the second passageway such that *ionized* molecules passing though the opening in the housing encounter the stream of drying gas before entering the second passageway.

4. The apparatus of claim 3 wherein the first and second voltage sources provide a voltage difference, whereby the difference urges the [charged] *ionized* molecules through the opening in the housing, across the stream of drying gas, and into the second passageway orifice.

5. The apparatus of claim 4 further comprising a third voltage source arranged adjacent to the exit of the first passageway, wherein the [electrospray] *electrosprayed aerosol* discharged from the first passageway is interposed between the third voltage source and the housing.

6. The apparatus of claim 3 wherein the first passageway comprises a needle and the second passageway comprises a capillary.

7. The apparatus of claim 6 wherein the [second passageway] *capillary* is heated.

8. The apparatus of claim 3 wherein the second passageway comprises an orifice.

9. The apparatus of claim 1 further comprising an analytical apparatus in fluid communication with the second passageway exit, wherein the housing is interposed between the first passageway and the analytical apparatus.

10. The apparatus of claim 9 wherein the analytical apparatus is capable of detecting and measuring the mass [and]-*to*-charge of *ionized* molecules which have been communicated from the second passageway exit into the analytical apparatus.

11. The apparatus of claim 10 wherein the analytical apparatus comprises a mass spectrometer.

12. The apparatus of claim 11 further comprising means for directing a stream of a drying gas in front of the second passageway orifice such that *ionized* molecules passing through the opening in the housing encounter the stream of drying gas before entering the second passageway.

13. The apparatus of claim 12 wherein the first and second voltage sources provide a voltage difference, whereby the difference urges the [charged] *ionized* molecules through the opening in the housing, across the stream of drying gas, and into the second passageway orifice.

14. The apparatus of claim 13 further comprising a third voltage source arranged adjacent to the exit of the first passageway, wherein the [electrospray] *electrosprayed aerosol* discharged from the first passageway is interposed[,] between the third voltage source and the housing.

15. The apparatus of claim 12 wherein the first passageway comprises a needle and the second passageway comprises a capillary.

16. The apparatus of claim 15 wherein the [second passageway] *capillary* is heated.

17. The apparatus of claim 12 wherein the second passageway comprises an orifice.

18. The apparatus of claim 4 further comprising a third voltage source arranged adjacent to the exit of the first passageway, wherein the third voltage source has an annular configuration and is positioned[,] such that the [electrospray] *electrosprayed aerosol* discharged from the first passageway is encircled by the third voltage source.

19. The apparatus of claim 13 further comprising a third voltage source arranged adjacent to the exit of the first passageway, wherein the third voltage source has an annular configuration and is positioned such that the [electrospray] *electrosprayed aerosol* discharged from the first passageway is encircled by the third voltage source.

*20. An apparatus for converting a liquid solute sample into charged molecules, comprising:*

*a first passageway having an exit for discharging an aerosol containing charged molecules, wherein said aerosol containing charged molecules has a center axis;*

*a second passageway for receiving said charged molecules from said first passageway, said second passageway having an entrance having a center axis, and arranged a distance from said exit of said first passageway, wherein an angle formed between said center axis of said aerosol containing charged molecules exiting said first passageway and said center axis of said entrance of said second passageway is about 75 degrees to about 105 degrees; and*

*a housing adjacent to said second passageway wherein a voltage source is connected to said housing.*

*21. The apparatus of claim 20 wherein a voltage source is connected to a passageway.*

*22. The apparatus of claim 20 wherein said angle is about 90 degrees.*

*23. The apparatus of claim 20 further comprising a gas source.*

*24. The apparatus of claim 20 wherein said second passageway for receiving said charged molecules from said first passageway is arranged so that said aerosol exiting from said first passageway substantially passes by said entrance of said second passageway.*

*25. The apparatus of claim 20 wherein said second passageway is arranged so that said charged molecules entering said entrance of said second passageway are substantially separated from said liquid solute of said sample.*

*26. The apparatus of claim 20 wherein said second passageway is arranged so that portions of said sample entering said entrance of said second passageway are substantially enriched in said charged molecules relative to said liquid solute of said sample.*

*27. The apparatus of claim 20 wherein said housing adjacent to said second passageway provides for directing a stream of a gas in front of said entrance of said second passageway and toward said aerosol.*

*28. The apparatus of claim 20 wherein a voltage source is connected to said first passageway, and said second passageway is at about ground potential.*

*29. The apparatus of claim 20 wherein a voltage source is connected to said second passageway, and said first passageway is at about ground potential.*

*30. The apparatus of claim 20 further comprising a second voltage source connected to an electrically conductive element for establishing a second electric field for creating an electrostatic force that influences said charged molecules in said aerosol to move in the direction of said entrance of said second passageway.*

*31. The apparatus of claim 20 wherein said first passageway comprises a needle.*

*32. The apparatus of claim 20 wherein said first passageway comprises a capillary.*

*33. The apparatus of claim 20 wherein said second passageway comprises a capillary.*

*34. The apparatus of claim 33 wherein said capillary is heated.*

*35. The apparatus of claim 20 wherein said second passageway comprises an orifice.*

*36. The apparatus of claim 20 further comprising an annular electrically conductive element encircling a portion of said first passageway and a second voltage source connected thereto for creating an electrostatic force that influences said charged molecules in said aerosol to move in the direction of said entrance of said second passageway.*

*37. An apparatus for converting a liquid solute sample into charged molecules, comprising:*

*a first passageway having an exit for discharging an aerosol containing charged molecules, wherein said aerosol containing charged molecules has a center axis;*

*a second passageway for receiving said charged molecules from said first passageway, said second passageway having an entrance having a center axis, and arranged a distance from said exit of said first passageway, wherein an angle formed between said center axis of said aerosol containing charged molecules exiting said first passageway and said center axis of said entrance of said second passageway is about 75 degrees to about 105 degrees; and*

*an electrically conductive element connected to a voltage source, wherein said element is arranged adjacent to said exit of said first passageway, wherein said aerosol exiting said first passageway is interposed between said element and said entrance of said second passageway.*

*38. The apparatus of claim 37 wherein said element is a plate.*

*39. The apparatus of claim 20 and further comprising an analytical instrument in fluid communication with an exit of said second passageway.*

*40. The apparatus of claim 39 wherein said analytical instrument is capable of detecting and measuring the mass-to-charge ratio of said charged molecules.*

*41. The apparatus of claim 40 wherein said analytical instrument comprises a mass spectrometer.*

*42. The apparatus of claim 20 wherein a voltage source is connected to said first passageway, and wherein said voltage sources are at different potentials.*

*43. The apparatus of claim 20 wherein a voltage source is connected to said second passageway, and wherein said voltage sources are at different potentials.*

*44. An apparatus for converting a liquid solute sample into charged molecules, comprising:*

*a first passageway having an exit for discharging an aerosol containing charged molecules, wherein said exit of said first passageway has a center axis;*

*a second passageway for receiving said charged molecules attracted from said first passageway, said second passageway having an entrance having a center axis, and arranged a distance from said exit of said first passageway, wherein an angle formed between said center axis of said exit of said first passageway and said center axis of said entrance of said second passageway is about 75 degrees to about 105 degrees; and*

*a housing adjacent to said second passageway wherein a voltage source is connected to said housing.*

*45. The apparatus of claim 44 wherein a voltage source is connected to a passageway.*

*46. The apparatus of claim 44 wherein said angle is about 90 degrees.*

*47. The apparatus of claim 44 further comprising a gas source.*

*48. The apparatus of claim 44 wherein said second passageway for receiving said charged molecules from said first passageway is arranged so that said aerosol exiting from said first passageway substantially passes by said entrance of said second passageway.*

*49. The apparatus of claim 44 wherein said second passageway is arranged so that said charged molecules entering said entrance of said second passageway are substantially separated from said liquid solute of said sample.*

*50. The apparatus of claim 44 wherein said second passageway is arranged so that portions of said sample entering said entrance of said second passageway are substantially enriched in said charged molecules relative to said liquid solute of said sample.*

*51. The apparatus of claim 44 further comprising a housing wherein said housing adjacent to said second passageway provides for directing a stream of a gas in front of said entrance of said second passageway and toward said aerosol.*

*52. The apparatus of claim 44 wherein a voltage source is connected to said first passageway and said second passageway is at about ground potential.*

*53. The apparatus of claim 44 wherein a voltage source is connected to said second passageway and said first passageway is at about ground potential.*

*54. The apparatus of claim 44 further comprising a second voltage source connected to an electrically conductive element for establishing a second electric field for creating an electrostatic force that influences said charged molecules in said aerosol to move in the direction of said entrance of said second passageway.*

*55. The apparatus of claim 44 wherein said first passageway comprises a needle.*

*56. The apparatus of claim 44 wherein said first passageway comprises a capillary.*

*57. The apparatus of claim 44 wherein said second passageway comprises a capillary.*

*58. The apparatus of claim 57 wherein said capillary is heated.*

*59. The apparatus of claim 44 wherein said second passageway comprises an orifice.*

*60. The apparatus of claim 44 further comprising an annular electrically conductive element encircling a portion of said first passageway and a second voltage source connected thereto for creating an electrostatic force that influences said charged molecules in said aerosol to move in the direction of said entrance of said second passageway.*

*61. The apparatus of claim 44 further comprising an analytical instrument in fluid communication with an exit of said second passageway.*

*62. The apparatus of claim 61 wherein said analytical instrument is capable of detecting and measuring the mass-to-charge ratio of said charged molecules.*

*63. The apparatus of claim 62 wherein said analytical instrument comprises a mass spectrometer.*

*64. The apparatus of claim 44 wherein a voltage source is connected to said first passageway, and wherein said voltage sources are at different potentials.*

*65. The apparatus of claim 44 wherein a voltage source is connected to said second passageway, and wherein said voltage sources are at different potentials.*

*66. An apparatus for converting a liquid solute sample into charged molecules, comprising:*

*a first passageway having an exit for discharging an aerosol containing charged molecules, wherein said exit of said first passageway has a center axis;*

*a second passageway for receiving said charged molecules attracted from said first passageway, said second passageway having an entrance having a center axis, and arranged a distance from said exit of said first passageway, wherein an angle formed between said center axis of said exit of said first passageway and said center axis of said entrance of said second passageway is about 75 degrees to about 105 degrees; and*

*an electrically conductive element connected to a voltage source, wherein said element is arranged adjacent to said exit of said first passageway, wherein said aerosol exiting said first passageway is interposed between said element and said entrance of said second passageway.*

*67. The apparatus of claim 66 wherein said element is a plate.*

* * * * *